(12) United States Patent
Tsai

(10) Patent No.: US 12,100,512 B2
(45) Date of Patent: Sep. 24, 2024

(54) MEDICAL IMAGE PROJECT MANAGEMENT PLATFORM

(71) Applicant: NATIONAL CHENG KUNG UNIVERSITY, Tainan (TW)

(72) Inventor: Yi-Shan Tsai, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 533 days.

(21) Appl. No.: 17/557,069

(22) Filed: Dec. 21, 2021

(65) Prior Publication Data

US 2023/0197268 A1  Jun. 22, 2023

(51) Int. Cl.
*G16H 50/20* (2018.01)
*G16B 50/30* (2019.01)
*G16H 30/20* (2018.01)
*G16H 30/40* (2018.01)
*G16H 80/00* (2018.01)

(52) U.S. Cl.
CPC .............. *G16H 50/20* (2018.01); *G16B 50/30* (2019.02); *G16H 30/20* (2018.01); *G16H 30/40* (2018.01); *G16H 80/00* (2018.01)

(58) Field of Classification Search
CPC ........ G16H 50/20; G16H 30/20; G16H 30/40; G16H 80/00; G16H 15/00; G16H 50/70; G16B 50/30
See application file for complete search history.

(56) References Cited

U.S. PATENT DOCUMENTS

| | | | | |
|---|---|---|---|---|
| 2020/0094072 A1* | 3/2020 | Ritter | ...................... | A61N 5/103 |
| 2020/0303062 A1* | 9/2020 | Tao | ........................ | G06N 99/00 |
| 2022/0284584 A1* | 9/2022 | Lee | .......................... | G06V 10/82 |
| 2022/0346659 A1* | 11/2022 | Ma | .......................... | A61B 5/055 |
| 2022/0392641 A1* | 12/2022 | Yuille | .................. | G06T 7/0014 |
| 2024/0221158 A1* | 7/2024 | Sasaki | ..................... | G06V 10/44 |

* cited by examiner

*Primary Examiner* — Fayyaz Alam
(74) *Attorney, Agent, or Firm* — WPAT, P.C

(57) ABSTRACT

The present invention discloses a medical image project management platform comprising a project management module and a radiomic feature extracting module. The project management module comprises a multi-module management interface and a labeling unit. An image is input by the multi-module management interface and received by the labeling unit. A first labeled image and a second labeled image are produced thereafter. The radiomic feature extracting module comprises an analysis unit and a feature extracting module. The analysis unit analyzes the first labeled image and gives the first labeled image a first labeling unit. The analysis unit analyzes the second labeled image and gives the second labeled image a second labeling unit. The radiomic feature extracting unit receives the first and the second labeling units and proceeds radiomic computation to output a radiomic feature.

20 Claims, 13 Drawing Sheets

MEDICAL IMAGE PROJECT MANAGEMENT PLATFORM

BACKGROUND

Field of Invention

The present invention is related to a project management platform, mainly associated with a project management platform incorporating radiomics and AI-assisting labeling.

Description of Related Art

The development of medical images has tremendously transformed clinical cancer therapy. With the digitalization of medical images and rapid growth of data volume, current development aims at the collection of multi-dimensional patient information and big data to further research of heterogeneity analysis of tumors. Solid tumors exhibit spatial and time heterogeneity from genetic, protein, cellular microenvironmental, tissue, or organ perspectives, limiting accuracy and representative of test results from invasive tests such as pathology, histology, or molecular biology.

In one aspect, through medical images, medical personnel can perform a comprehensive, non-invasive and quantitative observation of entire cancer morphology to monitor cancerous progression and reaction to therapy in real time, which provides reliable solutions for issues of tumor heterogeneity. Meanwhile, in radiomics, changes in transcriptional or translational patterns at the micro-level are postulated to be expressed in radiomic characteristics at the macro-level. Therefore, radiomics progressively develop into "extracting massive features from radiography in a high-throughput manner and transforming radiomic data into minable data with high resolution by automatic or semi-automatic methods." To establish the primary automatic or semi-automatic methods, in addition to professional expertise, deep-learning technology is also required. A new issue of integrating medical images and artificial intelligence will be introducing AI training, algorithm, validation, identification, and assisting clinical diagnosis.

Disclosed in Chinese Pat. No. CN111584046A is a medical image data AI processing method comprising firstly obtaining the image data and clinical data of the pre-diagnosis part of the patient, and then pre-processing the received image data and clinical data, obtaining the pre-processed image data and clinical data, then constructing artificial intelligence model and statistical model, analyzing and processing the pre-processed image data and clinical data; at last, based on the processing result of the artificial intelligence model and the statistical model, classifying the disease of the pre-diagnosis part of the patient, realizing fast and effectively analyzing the focused characteristics in the related image data. The invention can effectively and quickly assist the doctor's daily clinical diagnosis and identification diagnosis work in the image department. An AI model and a statistical model are disclosed in this patent for performing image labeling and training Still, there is no assistance in integrating diagnostic information for user data mining or project progress management.

Disclosed in PCT Pat. No. WO2021067624A1 are systems, methods, and software for providing a platform for AI-assisted medical image interpretation and report generation. One or more subsystems capture user input such as eye gaze and dictation for automated generation of clinical findings. Additional features include quality metric tracking and feedback, a worklist management system, and communications queueing. Natural language processing is introduced in this patent, but medical image labeling or radiomics are not disclosed. The purpose of this patent is to assist users in evaluating the results of decoded images. Evaluation and interpretation eventually rely on users but not image analysis by AI systems through automatic learning.

Disclosed in Chinese Pat. No. CN110033859A is a method for evaluating medical examination results of the patient, systems, program, and storage mediums. The medical inspection result comprises at least one image data set of the patient and at least one inspection report written in the natural language; the method consists of the following steps: providing a medical body that includes a plurality of medical concepts present in a majority of image data sets and a plurality of inspection reports of a plurality of patients; using at least one first analysis algorithm to analyze at least one image data set, to detect the medical concept of the medical ontology and marking the detected medical concept in the result data structure of the reference medical ontology; the first analysis algorithm is an artificial intelligence algorithm; using at least one second analysis algorithm to analyze at least one inspection report, to detect the medical concept of the medical ontology and mark the detected medical concept in the result data structure; the second analysis algorithm is a natural language processing algorithm; The result data structure is provided to at least one evaluation application of the processing medical concept. Disclosed in this patent is a technology involving NLP and image labeling, but radiomics is not applied. The analytic method using image datasets does not provide a solution for validating the accuracy of medical images generated from various patients, course of diseases, and experience of labeling personnel.

SUMMARY

The present invention discloses a medical image project management platform comprising: a project management module comprising a multi-module management interface for inputting an image, a labeling unit connecting to the multi-module management interface for receiving the image to produce a first labeled image and a second labeled image from the image; and a radiomic feature extracting module comprising an analysis unit connecting to the labeling unit for analyzing the first labeled image to output a first labeling unit, and analyzing the second labeled image to output a second labeling unit; and a feature extracting module connecting to the analysis unit for receiving the first labeling unit and the second labeling unit to perform a radiomic computation for outputting a radiomic feature.

Preferably, the foregoing platform further comprises a medical database connecting to the multi-module management interface. Preferably, the medical database comprising PACS, RIS, HIS, LIS, NIS.

Preferably, the foregoing platform further comprises a text extracting module connecting to the multi-module management interface and the medical database to receive the first diagnostic information from the multi-module management interface and extract the first text information from the first diagnostic information.

Preferably, the text extracting module further analyzes the first text information referring to the medical database so as to obtain a first categorized diagnosis.

Preferably, the first diagnostic information comprises a case history, a medical record, a biochemical analysis report, a biochemical test report, a molecular test report, or a heading of a medical image.

Preferably, the foregoing platform further comprises a labeling validation module connecting the radiomic feature extracting module for receiving the first labeling unit and the second labeling unit to perform a validation computation to produce a first validation result based.

Preferably, the labeling validation module comprises an overlapping validation model, wherein the labelling validation module performs a validation computation to produce the first validation result based on the overlapping validation model.

Preferably, the first validation result comprises a labeling qualification value, wherein the labelling qualification value comprises an ASSD (Average Symmetric Surface Distance) value, an IoU (Intersection over Union) value, a DICE coefficient, or a combination of two or more thereof.

Preferably, the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

the IoU value is computed according to the following formula:

$$IOU(LU1, LU2) = \frac{|LU1 \cap LU2|}{|LU1 \cup LU2|};$$

the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

Preferably, the platform further comprises an AI training module connecting to the labeling unit and the feature extracting module for reading the radiomic feature to train the labeling unit to establish an AI-assisting labeling model, wherein the labeling unit further connects to the medical database for the input of a third image from the medical database to automatically output a third labeled image via the AI-assisting labeling model.

Preferably, the text extracting unit connects to the AI training module to read the first categorized diagnosis and integrate the diagnosis and the radiomic feature into an AI medical diagnosis model.

Preferably, a diagnosis report is an input through the multi-module management platform, wherein the diagnosis report comprises second diagnostic information and a fourth image; the project management module matches the diagnosis report to produce an auto-labeled report based on the AI medical diagnosis model, wherein the auto-labeled report comprises a second categorized diagnosis and a fourth labeled image.

Preferably, the multi-module management interface visualizes information of each platform module so that a user retrieves, labels, or searches for medical data or project progress, wherein the medical data comprises a medical image or diagnostic information.

In another aspect, the present invention discloses a method for medical image project management comprising a radiomic feature extracting process, a text extracting process and a labelling qualification process, wherein the radiomic feature extracting process steps of: a first input step (S1-1): inputting a first image via a multi-module management interface; a labelling step (S1-2): receiving the image and producing a first labelled image and a second labelled image of the image via a labelling unit; an analysis step (S1-3): analyzing the first labelled image to output a first labelling unit and the second labelled image to output a second labelling unit via an analysis unit; and a feature extracting step (S1-4): receiving the first labelling unit or the second labelling unit for performing a radiomic computation so as to output a radiomic feature via a feature extracting module; the text extracting process comprises steps of: a second input step (S2-1): inputting a first diagnostic information to the text extracting module via the multi-module management interface; a text extracting step (S2-2): extracting a first text information from the first diagnostic information via the text extracting module; and a text categorizing step (S2-3): matching the first text information referring to the medical database for outputting a first categorized diagnosis, wherein the first diagnostic information comprises case history, medical record, a biochemical analysis report, a biochemical test report, a molecular test report or a heading of a medical image; and the labelling qualification process comprises receiving the first labelling unit and the second labelling unit for a validation computation to produce a first validation result via a labelling validation module, wherein the labelling validation module computes a labelling qualification value according to an overlapping validation model.

In one preferred embodiment, the first validation result comprises a labeling qualification value, wherein the labelling qualification value comprises an ASSD value, an IoU value, a DICE coefficient, or a combination of two or more thereof.

Preferably, the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

the IoU value is computed according to the following formula:

$$IOU(LU1, LU2) = \frac{|LU1 \cap LU2|}{|LU1 \cup LU2|};$$

the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

The medical image project management platform in the present invention demonstrates advantages as described below:
1. The present invention provides a one-station solution by incorporating data mining, application reviewing, progress management, image labeling, image integration, module training, E-alert, and E-assistance. The platform's operation is user-friendly and straightforward, and the process is easy and convenient.
2. The present invention performs the validation of medical image labeling quality. By calculating overlapping rates, labeling quality is validated, which assists personnel involved in image labeling adjust labeling patterns to optimize labeling quality.
3. Natural language processing (NLP) is applied in the present invention for disease categorizing and data mining of medical reports, which promotes the availability of information related to research topics of users.
4. AI-auto Annotation in the present invention allows intuitive labeling of PACS image, and radiomic feature of the image could be automatically exported. Radiomic feature, generated automatically from PACS, could be integrated and exported as DICOM or coordinates by the platform for various AI module training. The platform further provides Hospital-wide E-alert or E-assistance.

BRIEF DESCRIPTION OF THE DRAWINGS

The present invention can be more fully understood by reading the following detailed description of the embodiment, with reference made to the accompanying drawings as follows:

FIG. 11 illustrates test results of text extraction of example 2 in the present invention.

FIG. 12 illustrates test results of k-fold cross-validation of example 5 in the present invention.

DETAILED DESCRIPTION

According to the drawings, a group of particular embodiments of the invention is described in detail. Still, it shall be understood that the specific embodiments do not limit the protection scope of the invention.

The first embodiment in the present invention is a medical image project management platform (100) comprising a project management module (1) and a radiomic feature extracting module (2).

Figure 1A:
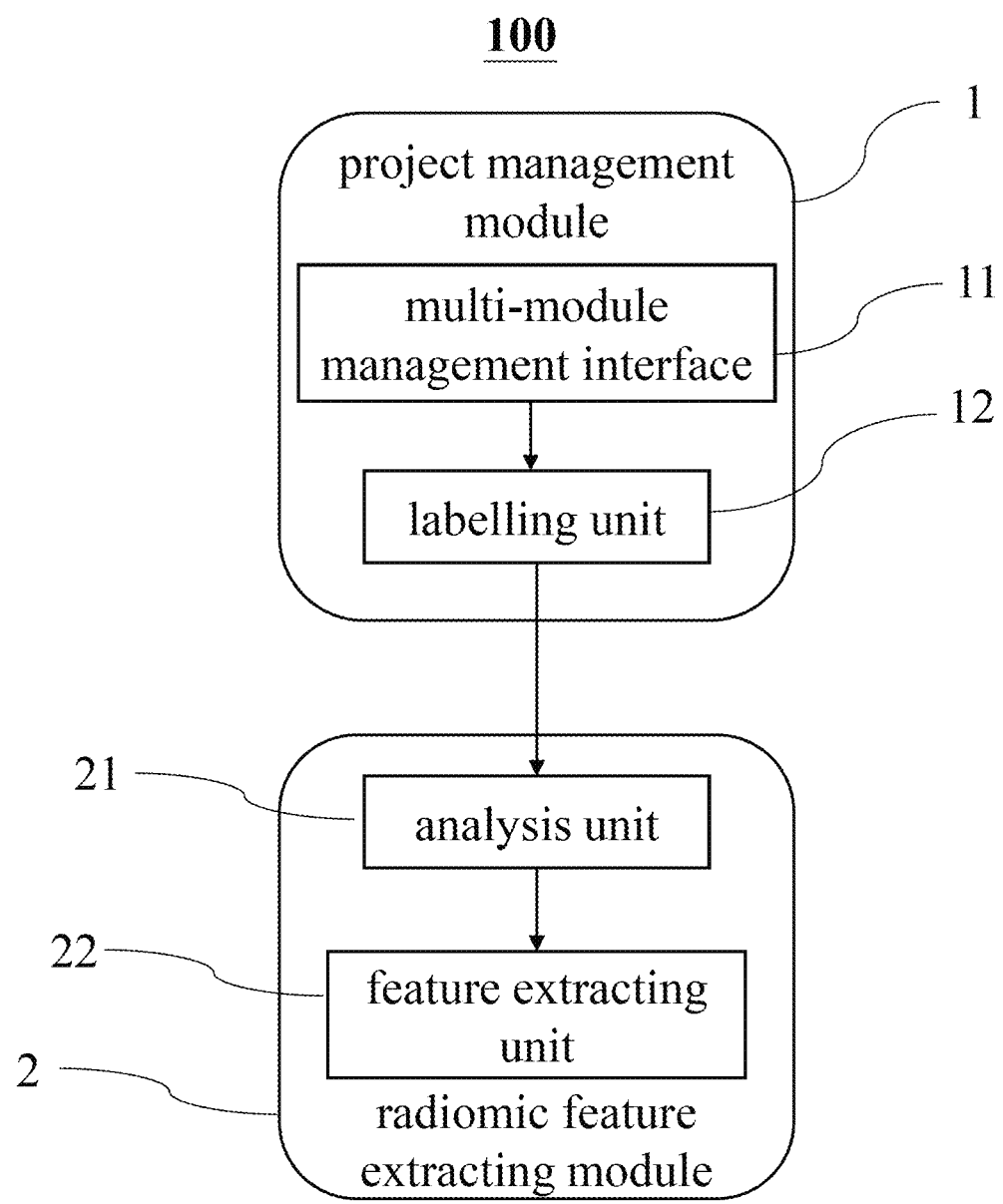
FIG. 1A is a block chart illustrating a configuration of a medical image project management platform of the first embodiment in the present invention.

Please refer to FIG. 1, a block diagram illustrating a configuration of the medical image project management platform (100) of the first embodiment in the present invention. According to FIG. 1, each module's interconnection and working principles are further elaborated. The project management module (1) comprises a multi-module management interface (11) for inputting an image and a labeling unit (12) connecting to the multi-module management interface (11) for receiving the image. A first labeled image and a second labeled image are produced from the image thereafter. The radiomic feature extracting module (2) comprises an analysis unit (21) connecting to the labeling unit to analyze the first labeled image to output a first labeling unit (LU1) and for analyzing the second labeled to output a second labeling unit (LU2). A feature extracting module (22) connecting to the analysis unit (21) for receiving the first labeling unit (LU1) and the second labeling unit (LU2) to perform a radiomic computation for outputting a radiomic feature.

Figure 1B:
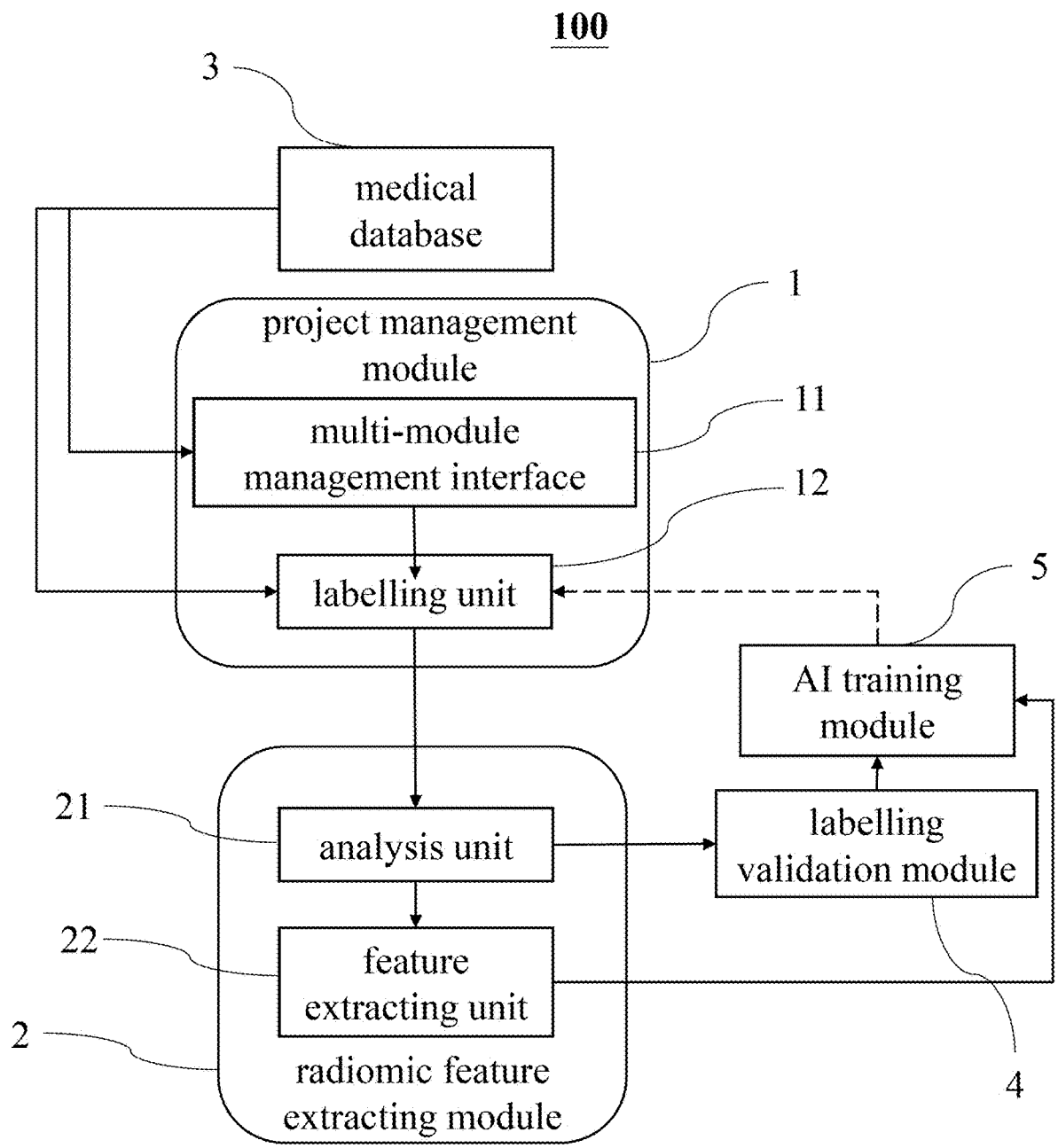
FIG. 1B is a block chart illustrating a configuration of a medical image project management platform of the second embodiment in the present invention.

Please refer to FIG. 1B illustrates the configuration of the medical image project management platform (100) of the second embodiment in the present invention, wherein the platform (100) further comprises a medical database (3) connecting to the multi-module management interface (11). Preferably, the medical database (3) comprises PACS, RIS, HIS, LIS, NIS.

Preferably, please further refer to FIG. 1B, the medical image project management platform (100) further comprises a labeling validation module (4), wherein the labeling validation module (4) comprises an overlapping validation model and connects to the analysis unit (21) for receiving the first labeling unit LU1 and the second labeling unit LU2 to perform a validation computation based on the overlapping model and produce a first validation result.

Preferably, the first validation result comprises a labeling qualification value, wherein the labelling qualification value comprises an ASSD (Average Symmetric Surface Distance) value, an IoU (Intersection over Union) value, a DICE coefficient, or a combination of two or more thereof, but not limited by this.

Preferably, the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

the IoU value is computed according to the following formula:

$$IOU(LU1, LU2) = \frac{|LU1 \cap LU2|}{|LU1 \cup LU2|};$$

and
the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

Specifically, the first labeling unit LU1 is a voxel coordinates coordinate which is extracted from the first labeled image by the radiomic feature extracting module (2); the second labeling unit LU2 is a voxel coordinates extracted from the second labeled image by the radiomic feature extracting module (2). The first labeling unit LU1 and the second labeling unit LU2 can be regarded as surface points of the first labeled image and the second labeled image, respectively. A surface point describes a particular voxel's coordinate, and the voxel is a voxel belonging to a different object in a neighboring area. Therefore, the specific voxel is defined as the surface point of the image.

Figure 2:
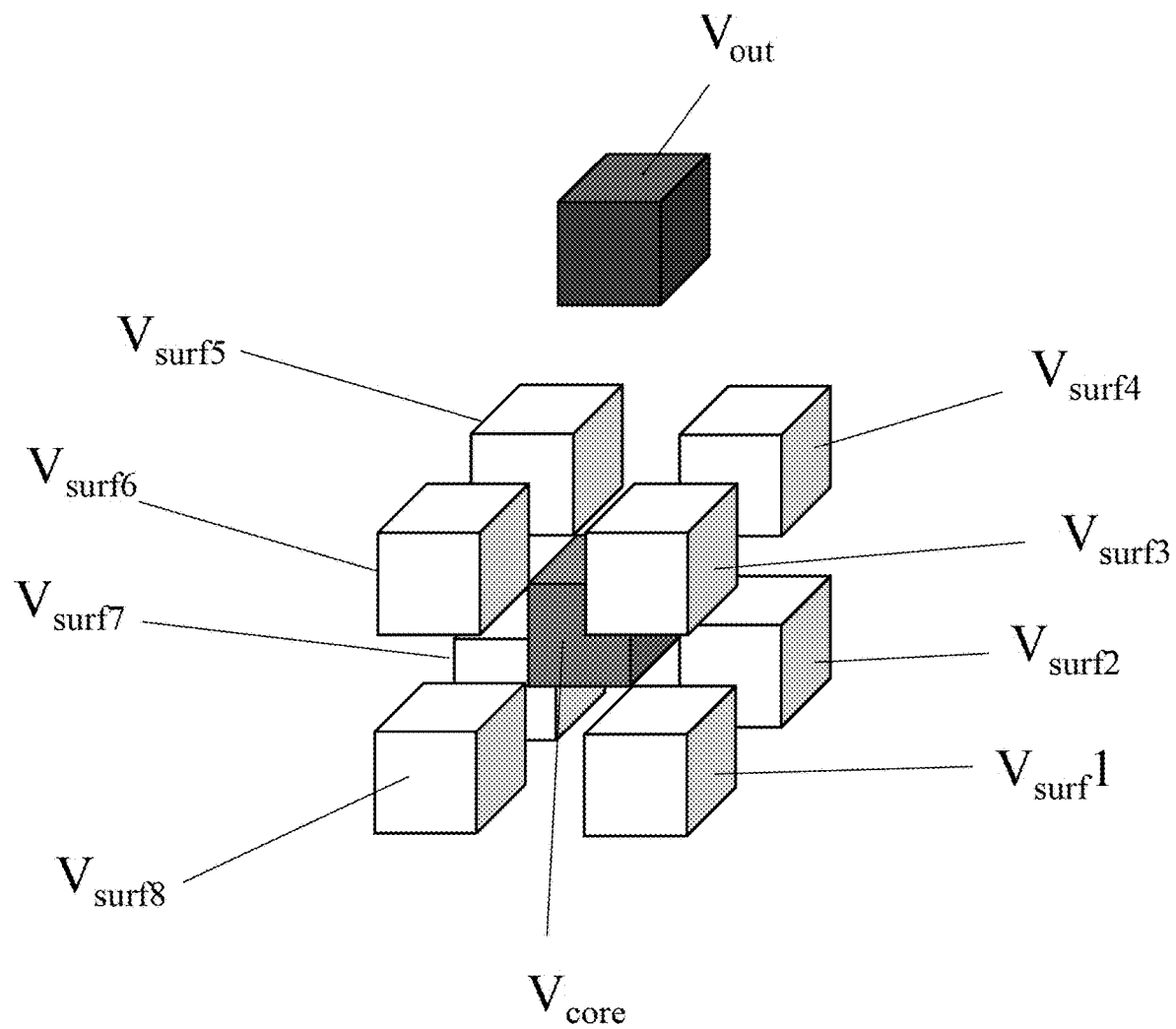
FIG. 2 illustrates the definition of the neighboring area of a specific voxel.

FIG. 2 is an example of the definition of a particular voxel in a neighboring area. $V_{core}$ represents a core voxel, and $V_{surf}1$, $V_{surf}2$, $V_{surf}3$, $V_{surf}4$, $V_{surf}5$, $V_{surf}6$, $V_{surf}7$, $V_{surf}8$ surround the $V_{core}$ to form a three-dimensional space of 3×3×3. Within the three-dimensional space, $V_{surf}1$, $V_{surf}2$, $V_{surf}3$, $V_{surf}4$, $V_{surf}5$, $V_{surf}6$, $V_{surf}7$, $V_{surf}8$ altogether define the neighboring area. When an outside voxel $V_{out}$ shows up, $V_{out}$ will be defined as a surface point since $V_{out}$ does not belong to the neighboring area.

Figure 3A:
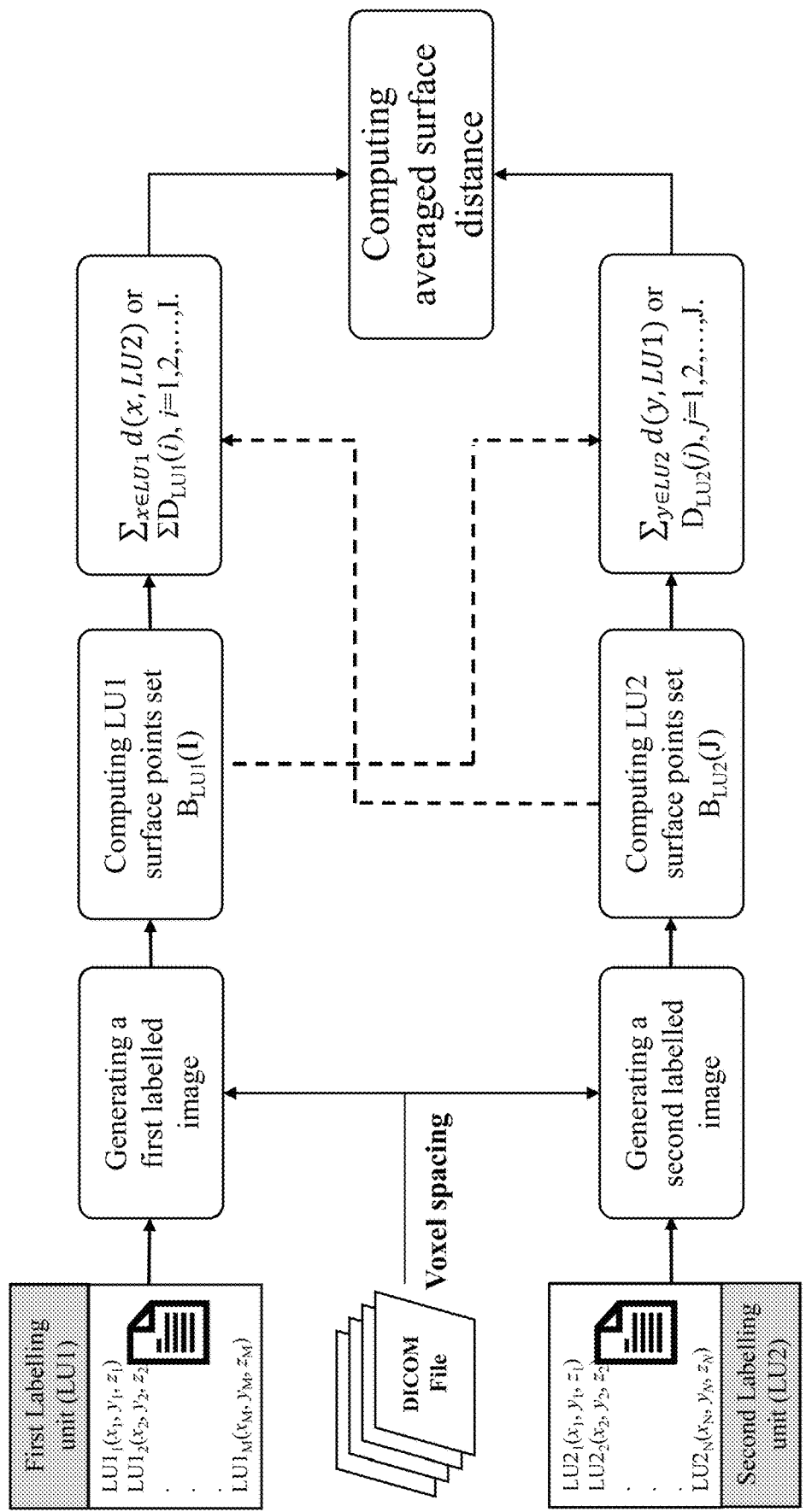
FIG. 3A is a flowchart to illustrate the algorithm of 3D overlapping validation.

FIG. 3A illustrates an algorithm of a 3D overlapping validation model. After the analysis, unit 31 receives the first labeling unit LU1 and the second labeling unit LU2, a first surface point set $B_{LU1}(I)$ and a second surface point set $B_{LU2}(J)$ are produced. The dotted line in FIG. 3A represents matching the first surface points set $B_{LU1}(I)$ and the second surface points set $B_{LU2}(J)$ by the analysis unit (21). To be more specific, when quantity I of surface points contained in the first surface points set $B_{LU1}(I)$ is different from quantity J of surface points contained in the second surface points set $B_{LU2}(J)$, the analysis unit (21) randomly selects and matches two surface points of shortest distance from the first surface points set $B_{LU1}(I)$ and the second surface points set $B_{LU2}(J)$ until one of the surface point sets are entirely matched. For instance, when I is fifty and J is one hundred, the analysis unit (21) performs subsequent computation of an average surface distance after fifty matches of surface points are done. The average surface distance includes an ASSD (Average Symmetric Surface Distance) value or an overlapping surface rate, wherein computation of the ASSD value accords to the following formula:

$$ASSD = \frac{1}{|LU1|+|LU2|} \times \left( \sum_{k \in LU1} d(x, LU2) + \sum_{y \in LU2} d(y, LU1) \right);$$

The overlapping surface rate is calculated according to the following formula:

$$\text{Surface overlapping rate} = \frac{\sum D_{LU1}(i) + \sum D_{LU2}(j)}{1+J}$$

Preferably, the first labeled image and the second labeled image are obtained by the same user labeling the image at different time points, different users labeling the image at different time points, or different users labeling the image simultaneously. For example, a user enters a liver tumor image via the multi-module management interface (11) and selects a region of interest (ROI) on the liver tumor image via the labeling unit (12). The multi-module management interface displays an ROI-1 on the liver tumor image. It transfers the labeled liver tumor image to the radiomic feature extracting module (2) for subsequent analysis and output of radimoics-1. After a couple of days, the user selects another region of interest on the liver tumor image via labeling unit (12). The multi-module management interface displays an ROI-2 on the liver tumor image. It transfers the labeled liver tumor image to the radiomic feature extracting module (2) for subsequent analysis and output of radimoics-2.

On the other hand, the analysis unit (21) receives and analyzes ROI-1 and ROI-2 to produce surface point coordinate sets Coordinates-1 and Coordinates-2, respectively. The labeling validation module (4) performs overlapping validation based on the surface coordinate sets and results in an ASSD value of 96.78%. Accordingly, the user can evaluate labeling qualities of the same image at different time points.

Preferably, the radiomic feature extracting module (2) creates voxels based on a convolutional network for image segmentation, U-Net, to acquire surface points of labeled images and produce surface point sets to calculate average surface distances. U-Net was firstly mentioned by Olaf Ronneberger, Phillip Fischer, and Thomas Brox in 2015. The structure of U-Net is a fully convolutional network without a fully connected layer. The network performs sampling under a first series based on convolution and Max Pooling and performs another sampling under a second series based on convolution and anti-convolution. Eventually, the first and second series are merged depending on a feature map (paths symmetrical to each series). As for the medical imaging field with a small data volume, the U-Net model is small with fewer parameters and therefore does not tend to overfit.

Preferably, the platform further comprises an AI training module (5) connecting to the labeling unit (12) and the feature extracting module (22) for reading the radiomic feature to train the labeling unit (12) to establish an AI-assisting labeling model, wherein the labeling unit (12) further connects to the medical database (3) for the input of a third image from the medical database (3) so that a third labeled image is output automatically based on the AI-assisting labeling model.

Preferably, the labeling validation value further comprises an IoU value and a DICE value, wherein the following formula calculates the IoU value:

$$IOU(LU1, LU2) = \frac{|LU1 \cap LU2|}{|LU1 \cup LU2|};$$

The following formula calculates the DICE value:

$$DICE(LU1, LU2) = \frac{2|LU1 \cap LU2|}{|LU1| + |LU2|}$$

In particular, users can calculate a ratio of IoU value and DICE value after multiple times of labeling. A labelling can be determined to be eligible as IoU/DICE ratio is more significant than a specific figure X and ineligible as IoU/DICE is less than X. Please refer to FIG. 3B for further illustrating the definition of IoU overlapping rate. For example, an area of overlap|LU1∩LU2| of the first labeling unit LU1 and the second labeling unit LU2 and an area of union|LU1∪LU2| of the first labeling unit LU1 and the second labeling unit LU2 are both calculated. A first overlapping rate of both the labeling units is calculated according to the IoU formula as stated above. After that, a second overlapping rate of both the labeling units is calculated according to the DICE formula mentioned above. The ratio of the first and the second overlapping rate is defined as a reference value for image labeling quality but not limited by this. In another aspect, IoU or DICE's value can be individually considered a validity index of 2D image overlapping rate.

Figure 3B:
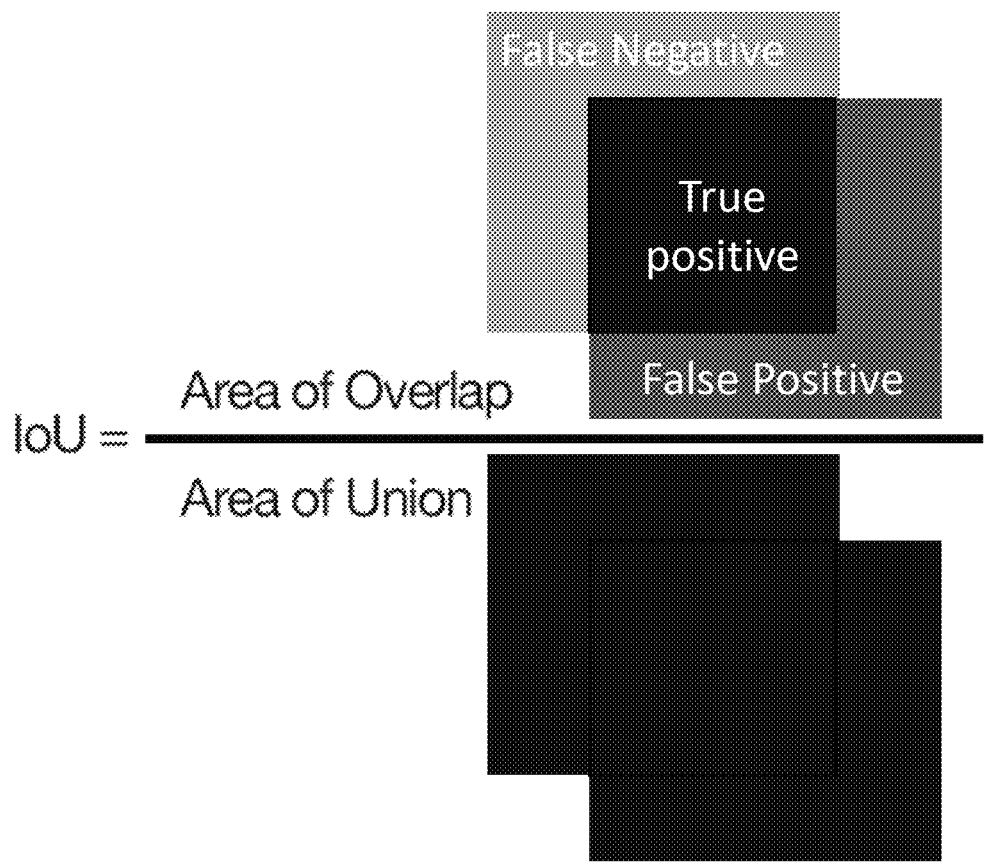
FIG. 3B illustrates the definition of the IoU overlapping rate.

To be specific, please continue on FIG. 3B, a True Positive (TP) is defined by the overlap of first labeling unit LU1 and second labeling unit 2 (LU2), a False Negative (FN) is determined by the area of LU1 outside an area of LU1 and LU2 overlap, and a False Positive (FP) is defined by the area of LU2 outside an area of LU1 and LU2 overlap. Based on the values mentioned above, a DICE value can be calculated through an F1-score formula, while the F1-score formula is derived from the following equations:

Equation (1): Precision;

$$\text{precision} = \frac{TP}{TP + FP} = \frac{|LU1 \cap LU2|}{|LU2|} \quad (1)$$

Equation (2): Recall;

$$\text{recall} = \frac{TP}{TP + FN} = \frac{|LU1 \cap LU2|}{|LU1|} \quad (2)$$

Equation (3): Equations (1) and equation (2) are substituted into equation (3) to calculate F1-score.

$$F1 = \frac{2}{\frac{1}{\text{precision}} + \frac{1}{\text{recall}}} = \frac{2|LU1 \cap LU2|}{|LU1| + |LU2|} \quad (3)$$

Figure 4:
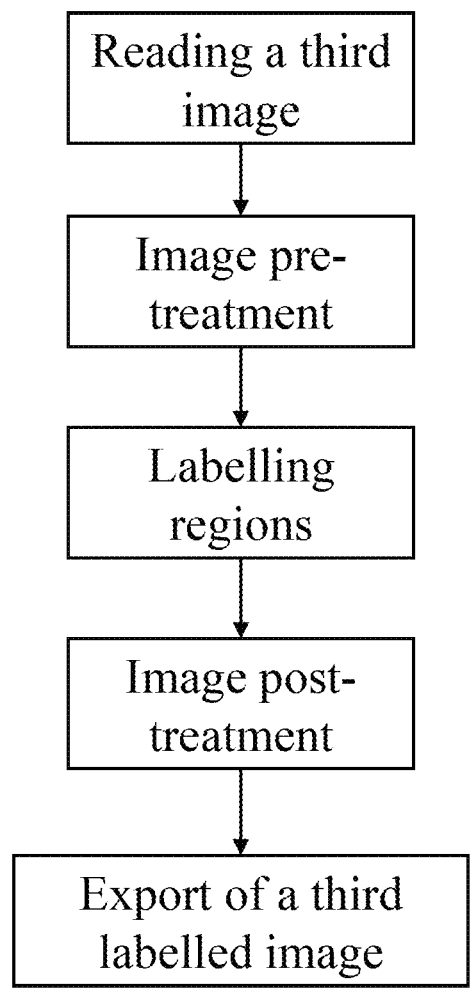
FIG. 4 is a flowchart to illustrate the algorithm of image labeling of the second embodiment.

Preferably, the AI-assisting labeling model labels the third image according to an image labeling algorithm to produce the third labeled image for assisting users to label images. Please refer to FIG. 4, a flowchart to illustrate the image labeling algorithm. The algorithm comprises that a third image is read and undergoes an image pre-treatment. A user selects a labeled region subjecting to an image post-treatment to produce a labeling result and output the third labeled image. Furthermore, via the multi-module management interface (11) users could check whether labeling the third labeled image is accomplished or the labeled region passes labeling quality validation.

More preferably, the image pre-treatment comprises CLAHE (Contrast Limited Adaptive Histogram Equalization) image process. CLAHE image process adjusts image contrast through a self-adaptive histogram equalization method. The image post-treatment comprises an image morphological process. The morphological image process includes erosion, dilation, opening, and closing. Specifically, erosion aims to reduce the data volume of raw images and filtrates noise by erosion algorithm.

In contrast to erosion, dilation reinforces the image by detecting image parameters. In case that the image is processed by erosion or dilation process and results that data volume of deletion or compensation is larger than raw data, opening and closing processes are required for subsequent adjustments. The opening performs erosion before dilation, while the closing performs dilation before erosion.

Figure 5:
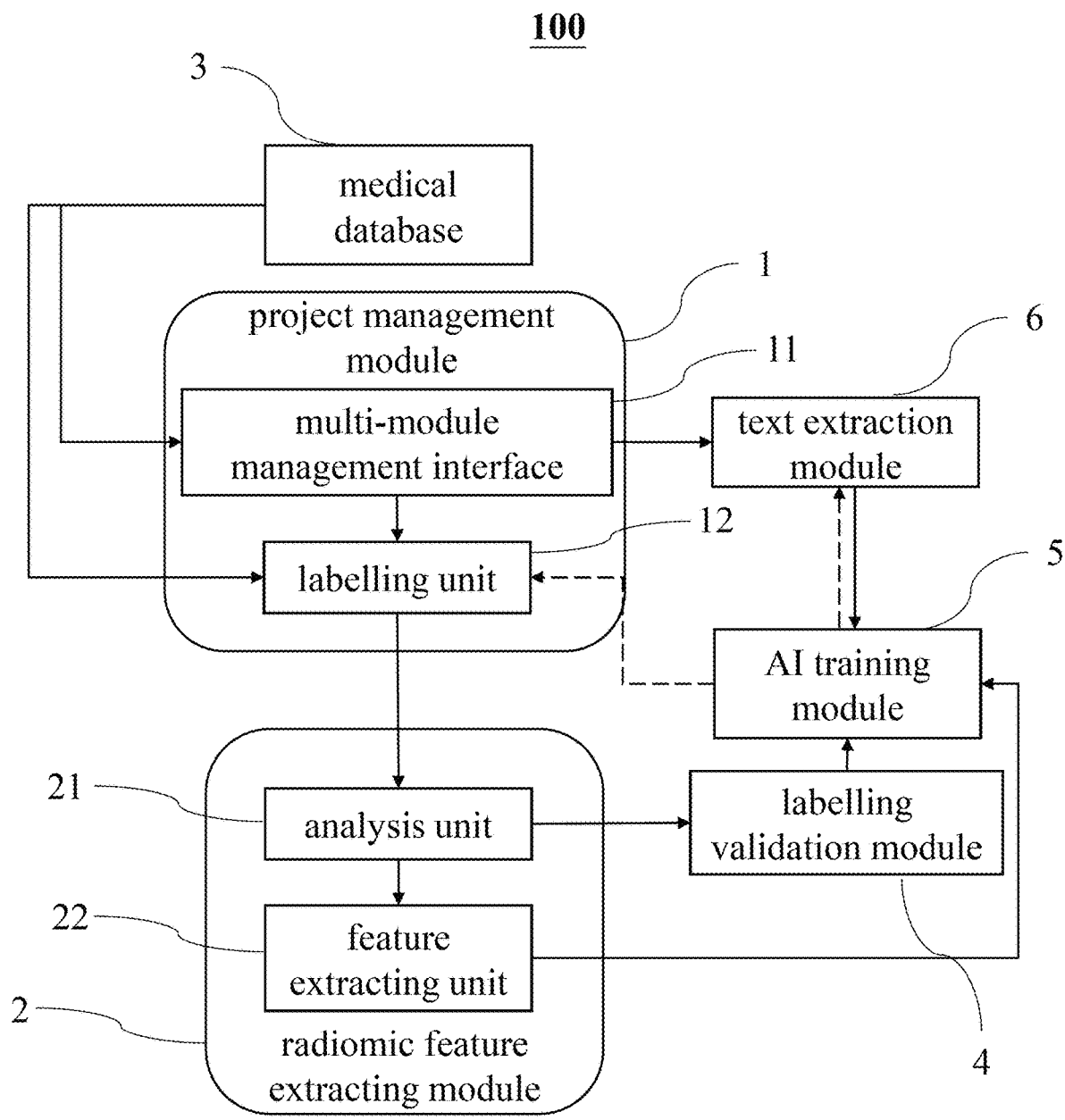
FIG. 5 is a block chart illustrating a configuration of a medical image project management platform of the second embodiment in the present invention.

Please refer to FIG. 5, a block chart illustrating a configuration of the medical image project management platform (100) of the third embodiment in the present invention. In the third embodiment, the medical image project management platform (100) further comprises a text extracting module (6) connecting to the multi-module management interface (11) and the medical database (3) for receiving the first diagnostic information from the multi-module management interface (11) and extracting a first text information from the first diagnostic information. The text extracting module (6) analyzes the first text information referring to the medical database (3) to obtain the first diagnosis categorized result, wherein the first diagnostic information comprises case history, medical record, a biochemical analysis report, a biochemical test report, a molecular test report or a heading of a medical image.

The text extracting module (6) performs a text categorizing process of digitalized medical data relying on a keyword search model based on natural language processing (NLP). For instance, the medical image project management platform (100) imports hematology reports from the medical database (3) and performs a text categorizing process through the text extracting module (6). The keyword search model categorizes hematology reports into bone marrow smear reports, bone marrow pathology reports, chromosome reports, and cell marker reports. More preferably, the medical image project management platform (100) archives images in correspondence to each categorized report, such as CT scan or X-ray photography.

Preferably, fundamental elements of the keyword search algorithm are based on regular expression and negative words determination; to further specify it, the regular expression is a method for string processing. Users can define string rules based on regular expression and search for strings corresponding to text string rules. As for negative words determination, users customize negative words of frequent use in advance, such as "no," "not," "without." Subsequently, texts containing keywords are further matched through a regular expression and confirmed whether negative words are identified within the texts. If negative words are identified in one text, such a text is determined as a non-target text and excluded from the categorized texts.

Figure 6:
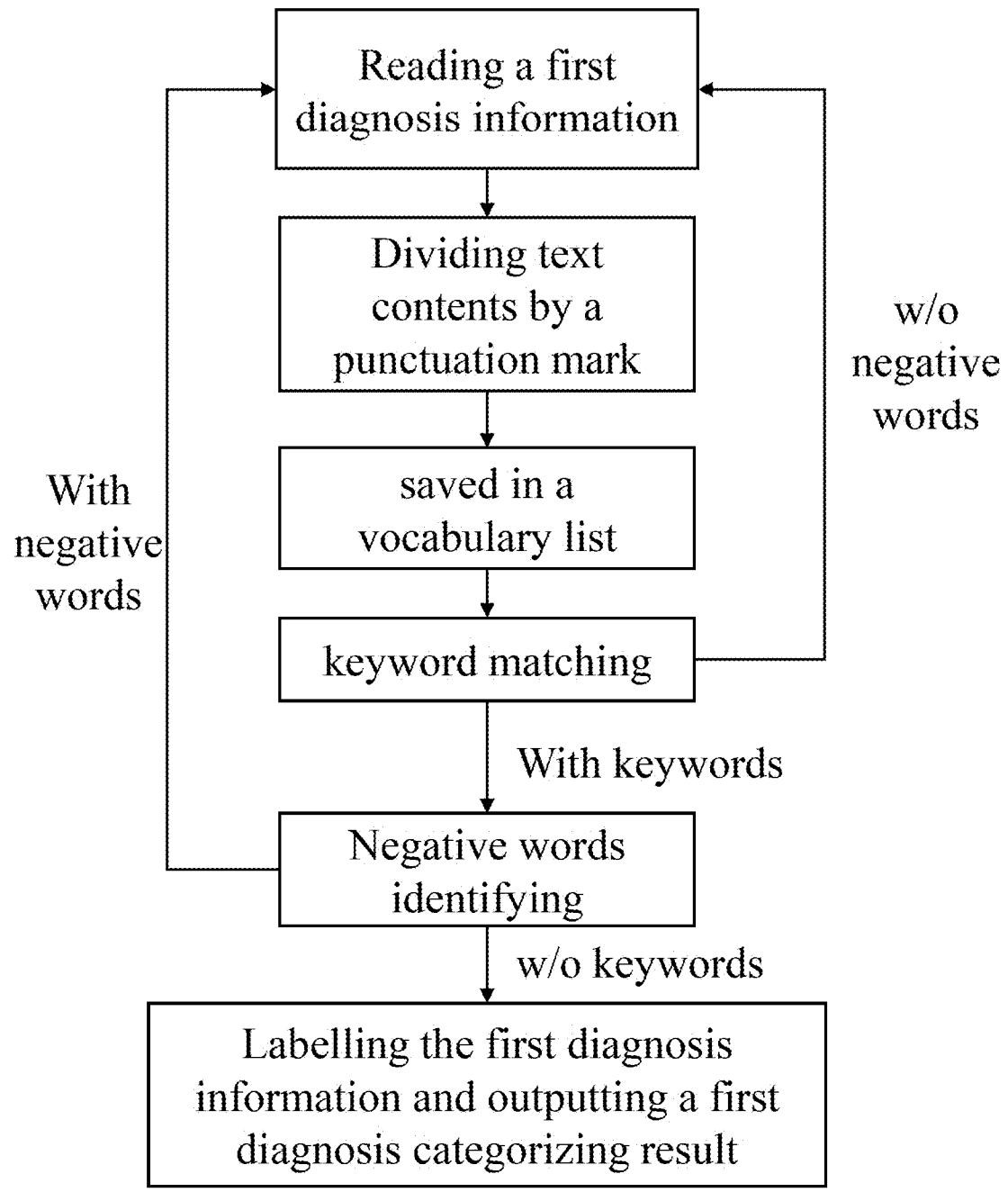
FIG. 6 is a flowchart illustrating a search algorithm based on Natural Language Processing.

As for working principles for the NLP keyword search model, please refer to FIG. 6 illustrating the natural language processing algorithm (NLP). First of all, the text extracting module (6) reads a first diagnostic information and divides contents of the first diagnostic information according to a punctuation mark. The divided contents are further saved in a vocabulary list. Secondly, keyword matching and searching are performed depending on the definition of the aforementioned regular expression. If there is no keyword, the module returns to reading a first diagnostic information. If there are keywords, a first text information is output, and a negative words determination is carried out. Subsequently, when there are no negative words, a text mark is given to the first text information, and a first diagnosis categorized result is output, wherein the first diagnosis categorized result comprises case history, medical report, image analysis report, and the punctuation marks comprise period, comma or other common punctuation marks.

Preferably, when users define keywords through a regular expression, a rule table is created through the multi-module management interface (11). Table 1 is an example to illustrate a basic structure of the rule table, but not limited by this.

TABLE 1

| Name of rule table: Cellularity-percentage | |
| --- | --- |
| Report | BMA |
| Heading | Interpretation |
| Keywords | Cellular |
| Return type | Number % |
| negative | — |

In the example as mentioned above, Cellularity-percentage is regarded as the input source of the first diagnostic information and is further divided in details as stated below:

1) Report: report types in search are regraded; bone marrow aspiration (BMA) is set as report type in this example.
2) Heading: headings of first text information in search are regarded. According to headings, report types are identified, and "interpretation" is set as the target heading in this example.
3) Keywords: keywords of first text information in search are regarded. Keywords are used for filtering first text information screened by the aforementioned heading, and Cellular is set as a keyword in this example.
4) Return type: data format of the report type of first text information in search are regarded. When the return type is set, the text extracting module (6) captures numbers or words, and Number % is set as capture subject in this example.
5) Negative: users customize whether default negative words are required in this example so that the text extracting module (6) performs text extraction aiming at negative words. There are no default negative words setting in this example.

Preferably, the text extracting module (6) further comprises a text dividing component to determine the location of the punctuation mark in texts and defines the attribute of the punctuation mark, wherein the text dividing component comprises a Natural Language Tool Kit (NLTK). For example, please refer to TABLE 2, which illustrates the text contents of the first diagnostic information and divides results in this example; the first diagnostic information is a medical report in English. Array A is raw contents of the report before the text dividing process; array B is text contents after text dividing according to periods; array C is text contents after dividing by periods anterior to determination by text dividing component. In particular, users customize keywords and negative words through the rule mentioned above table and leave them for text dividing component for further determination. In this example, the text dividing component identifies a period of "Susp." to be an abbreviation mark and determines "Susp. Osteoporosis with compression fracture of L1." as a customized dividing pattern, and thus contents of array C are produced.

TABLE 2

| | | Text dividing results |
| --- | --- | --- |
| A | Raw contents | Degenerative disc disease, L1-2, and L3-4. Susp. Osteoporosis with compression fracture of L1. Spondylosis and kyphoscoliosis. S/P Cholecystectomy. Vascular calcifications. |
| B | Dividing by periods | Degenerative disc disease, L1-2, and L3-4. Susp. Osteoporosis with compression fracture of L1. Spondylosis and kyphoscoliosis. S/P Cholecystectomy. Vascular calcifications. |
| C | Dividing by Text dividing component | Degenerative disc disease, L1-2, and L3-4. Susp. Osteoporosis with compression fracture of L1. — Spondylosis and kyphoscoliosis. S/P Cholecystectomy. Vascular calcifications. |

Specifically, NLP is based on Name Entity Recognition (NER). In particular to the NER task, a masked token is predicted by a MLM task used by the pre-trained BERT, and a label belonging to the token is predicted, and a text labeling vector is an output. Then, through linear transformation, a NER classifier reduces dimensionalities of multi-dimensional vectors exported by BERT to a low-dimension vector corresponding to NER, wherein the token comprises an individual word, a part of an individual word, punctuation marks, terms or phrases, and the token originates from a basic unit produced from the given text divided by the text extracting module (6). Subsequently, the token is transformed into digital vectors to be input into the model for categorization or analysis.

Figure 7:
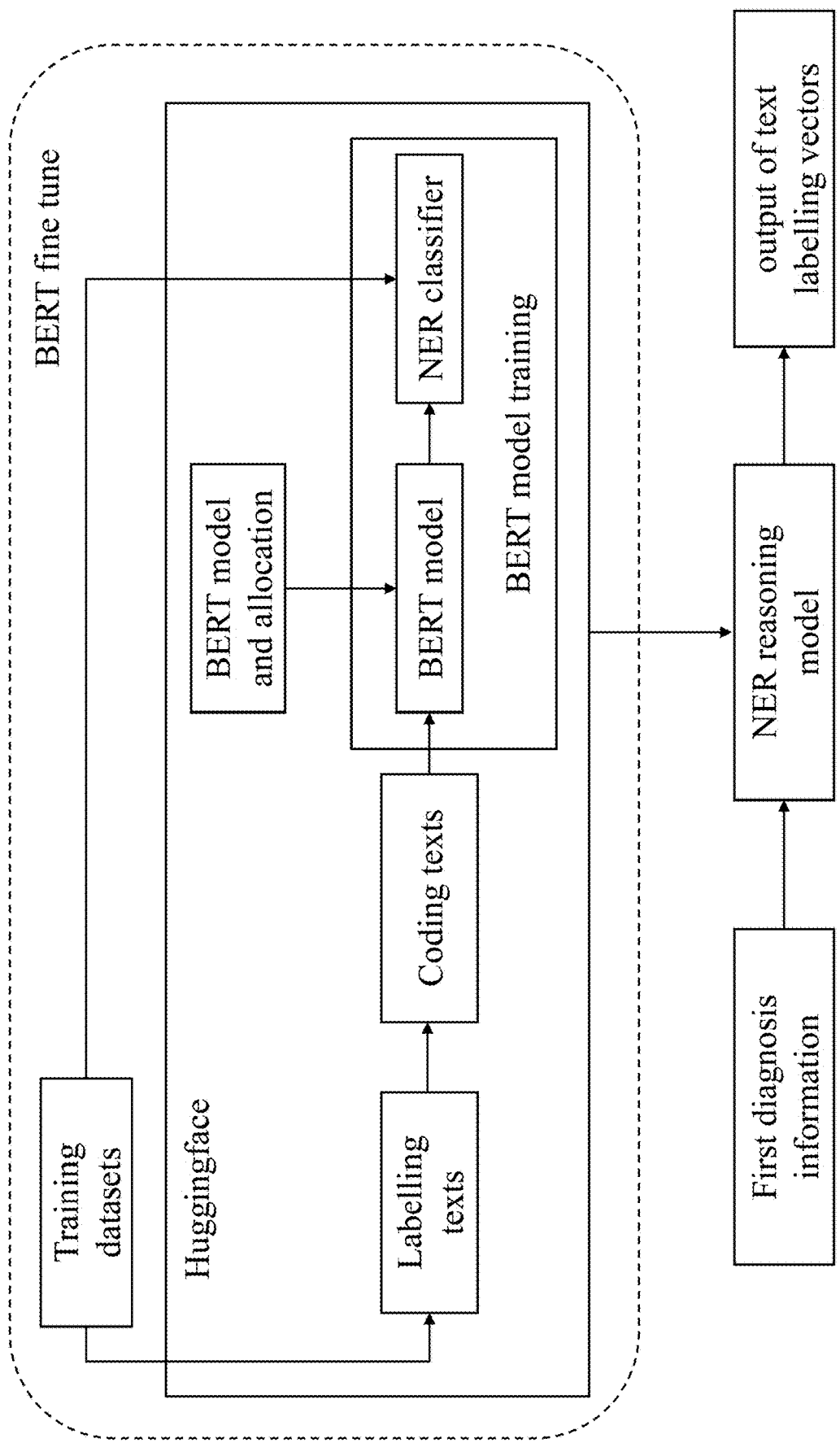
FIG. 7 is a flowchart illustrating a preferable example of the third embodiment to use API of Huggingface for generating text labeling vector.

More preferably, an attention mask is taken as a fundament of computing mechanism, which is a computing pattern corresponding to attention mechanism, and value of each element is 0 or 1. If the token is masked or used as a filling element, the token is not necessarily computed through the attention mechanism, and the value is 0. If the token corresponds to various test sequences, it is exemplified that NSP tasks require the input of two text sequences, and a text coding is conducted. In one preferable example, please refer to FIG. 7, API provided by Huggingface is further utilized for assisting users in training the labeled training data through the BERT model, and therefore the processing is simplified. The labeled training data is collocated with the NER classifier for fine-tuning to generate a NER reasoning model. The text extracting module (6) extracts a first text information from a first diagnostic information for following comparison based on the NER reasoning model. Please refer to TABLE 3; in TABLE 3, detailed training parameter settings of BERT are illustrated.

TABLE 3

| Parameter | Parameter code | Setting |
| --- | --- | --- |
| Sequence length | sequence_length | 512 |
| Batch size | batch_size | 8 |
| Learning rate | lr | $5e^{-05}$ |
| Hidden dimension | hidden_dim | 768 |
| Fine-tune layer | fine-tune layer | 12 |

Preferably, the output format of the first diagnosis categorizing results can be customized through the multi-module management interface (11) according to anticipated categorizing results in collocation with the rule table. For example, the output format can be customized in reference to table structure as TABLE 4, but not limited by this.

TABLE 4

| Report type | Cellularity description | Cellularity percentage | M/E ratio |
| --- | --- | --- | --- |
| Bone marrow smear | Normal | 30% | 7:1 |
| Bone marrow pathology | Hypo | 25% | 6:7 |

Preferably, the multi-module management interface (11) visualizes information of each module of the platform (100) so that a user retrieves, labels, or searches for medical data or project progress, wherein the medical data comprises a medical image or diagnostic information.

Please continue to refer to FIG. 5; preferably, the text extracting module (6) connects to the AI training module (5) and reads the diagnosis categorizing result for integrating the diagnosis categorizing result and radiomic feature to generate an AI medical diagnosis model. Exemplarily, a user input a diagnosis report via the multi-module management platform 11, wherein the diagnosis report comprises second diagnostic information and a fourth image. Project management module (1) matches the diagnosis report based on the AI medical diagnosis model to generate an auto-labeled report. The auto-labeled report comprises a second diagnosis categorizing result and a fourth labeled image.

Figure 8A:
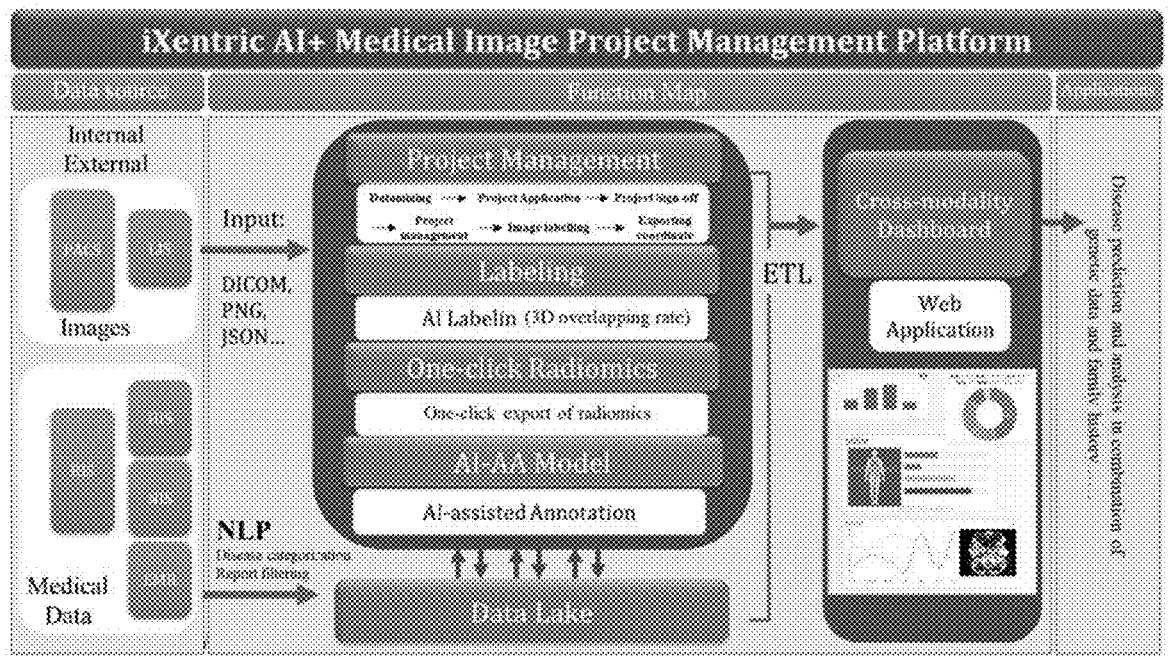
FIG. 8A is an exemplary configuration of a medical image project management platform of the third embodiment.
Figure 8B:
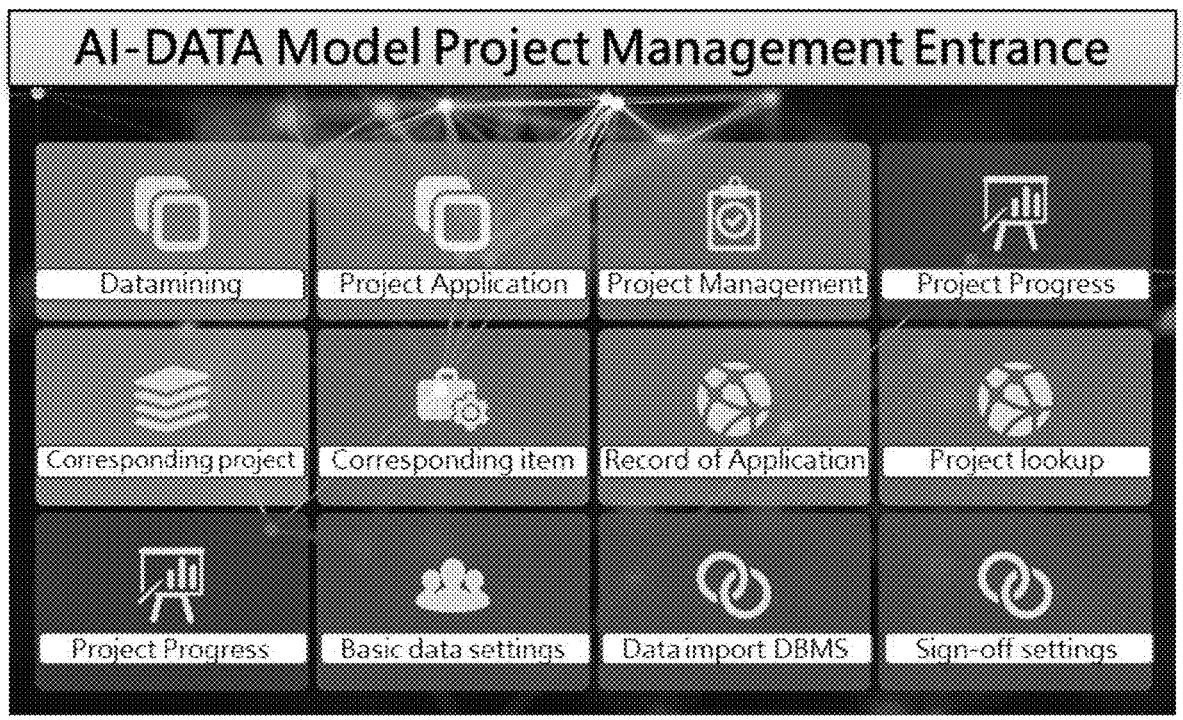
FIG. 8B is an exemplary configuration of a Cross-Modality Dashboard of the third embodiment.

More preferably, the multi-module management interface (11) further comprises the project application function, IRB certification auditory function, and PACS VIEWER. Through the interface, users can examine whether the imported project is IRB-certified and grant permission or withdrawal depending on project contents. The multi-module management interface (11) is configured for users to perform project management, including deleting or closing a project. On the other hand, exemplarily, PACS VIEWER allows users to select a project referring to a labeling list of tasks and perform image labeling. During the labeling process, under the collaboration of the labeling unit, the analysis unit, and the labeling validation module, the quality of image labeling is validated through an overlapping validation model. The multi-module management interface (11) further displays the validation value of labeling quality, and users further label images in reference to labelling quality validation value. Moreover, labeled image files, labeling units, and radiomic features are exported by the medical image project management platform (100). The labeled image files can be exported in DICOM format, labeling units are present in coordinates and exported as JSON files. On the other hand, radiomic features are exported in CSV format. The multi-module management interface (11) comprises a Cross-modality Dashboard that can be web-based. FIG. 8A illustrates a preferred exemplary configuration of the medical image project management 100 of the third embodiment. The medical image project management platform (100) integrates intuitive image labeling, auto-generation of radiomic features, disease categorization and data mining, image-integrating module training, and integrative AI-assisting labeling. The medical image project management platform (100) provides a one-station solution, an API that can be formulated to collect data in the data center via the Cross-modality Dashboard. Presentation forms of information can be customized by each user, and the dashboard is operated by intuitive dragging. FIG. 8B demonstrates a preferred exemplary configuration of the cross-modality dashboard of the third embodiment. The cross-modality dashboard incorporates multiple functions, including data mining, project application, project management, project progress, related project, corresponding item, application record, search for a project, basic data setting, data import or sign-off process setting, but not limited to this. The cross-modality dashboard allows users to select and operate any preceding functions. In one preferred example, customization of tasks on the cross-modality dashboard can be performed to meet the requirements of hospitals or concerned departments.

The fourth embodiment in present invention is a method for medical image project management. Please refer to FIG. 9, the method comprises a radiomic feature extracting process S1, a text extracting process S2, and a labeling qualification process S3, wherein the radiomic feature extracting process S1 comprises steps of:
  a first input step (S1-1): a first image is an input via a multi-module management interface;
  a labeling step (S1-2): the image is received, and a first labeled image and a second labeled image of the image are produced via a labeling unit;
  an analysis step (S1-3): the first labeled image is analyzed to output a first labeling unit LU1, and the second labeled image LU2 is analyzed to output a second labeling unit via an analysis unit; and
  a feature extracting step (S1-4): the first labeling unit or the second labeling unit are received for performing a radiomic computation to output a radiomic feature via a feature extracting module; and
the text extracting process S2 comprising steps of:
  a second input step (S2-1): a first diagnostic information is input to the text extracting module via the multi-module management interface;
  a text extracting step (S2-2): a first text information is extracted from the first diagnostic information via the text extracting module; and
  a text categorizing step (S2-3): the first text information is matched referring to the medical database for outputting a first categorized diagnosis, wherein the first diagnostic information comprises case history, medical record, a biochemical analysis report, a biochemical test report, a molecular test report or a heading of a medical image; and
the labeling qualification process S3 comprises receiving the first labeling unit LU1 and the second labeling unit LU2 for a validation computation to produce a first validation result via a labeling validation module. According to an overlapping validation model, the labeling validation module computes a labeling qualification value.

Preferably, the labeling qualification value comprises an ASSD value, an IoU value, a DICE coefficient, or a combination of two or more thereof, wherein the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

the IoU value is computed according to the following formula:

$$IOU(LU1, LU2) = \frac{|LU1 \cap LU2|}{|LU1 \cup LU2|};$$

and
the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

Figure 9:
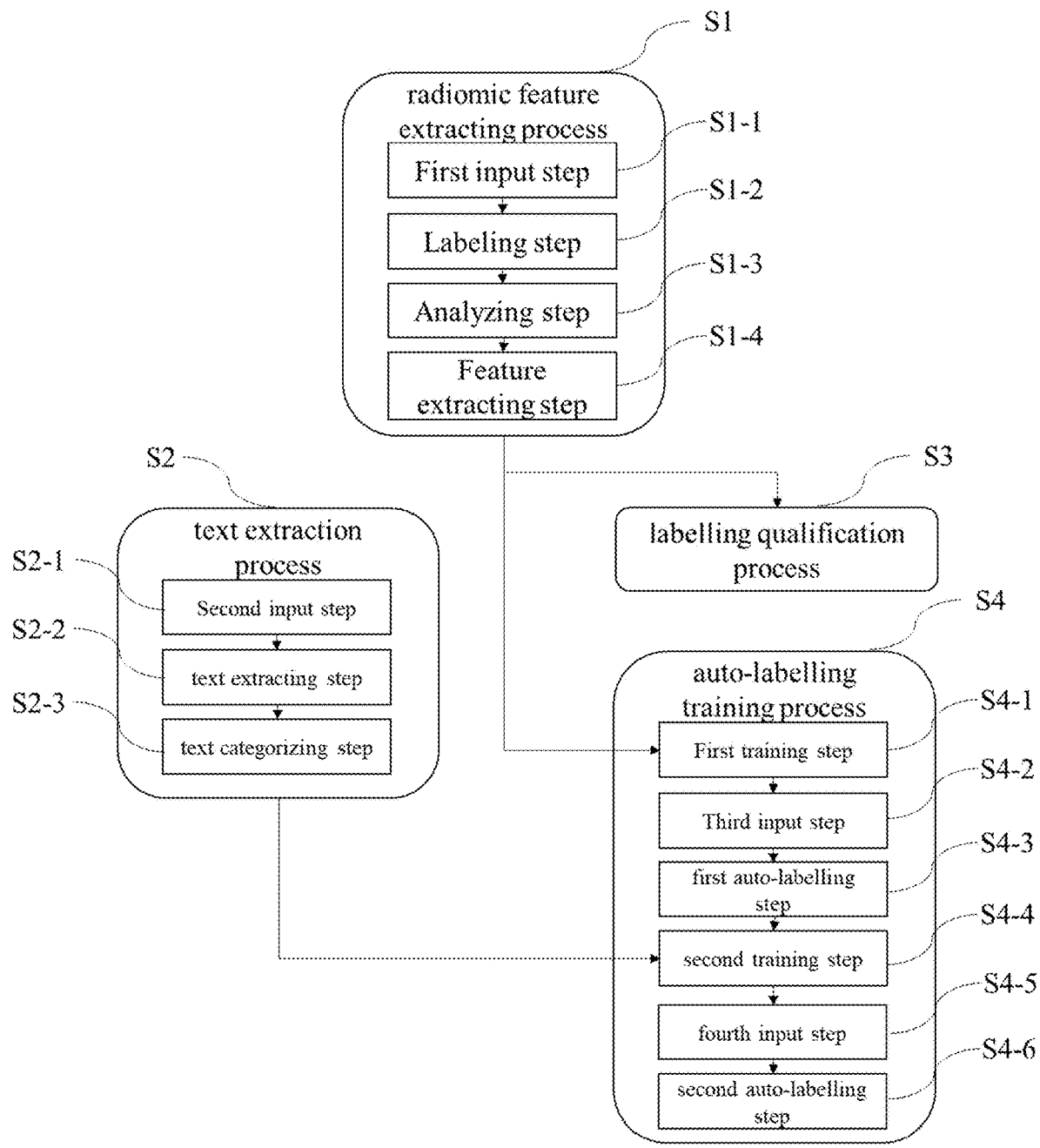
FIG. 9 is a flowchart to illustrate medical image project management method of the fourth embodiment in the present invention.

Please continue to refer to FIG. 9, more preferably, the medical image project management method further comprises an auto-labeling training process 4, comprising steps of:

- a first training step (S4-1): the radiomic feature is read by an AI-training module to train the labeling unit to establish an AI-assisting labeling model;
- a third input step (S4-2): a third image is an input to the medical image by the labeling unit;
- a first auto-labeling step (S4-3): a third labeled image is automatically generated by the labeling unit based on the AI-assisting labeling model;
- a second training step (S4-4): the first diagnosis categorizing result is read and integrated with the radiomic feature by the AI-assisting labeling model to establish an AI medical diagnosis model;
- a fourth input step (S4-5): a diagnosis report is input via the multi-module management platform, wherein the diagnosis report comprises a second diagnostic information and a fourth image;
- a second auto-labeling step (S4-6): the project management module compares the diagnosis report based on the AI medical diagnosis model to generate an auto-labeling report, wherein the auto-labeling comprises a second diagnosis categorizing result and a fourth labeled image.

Example 1

Figure 10:
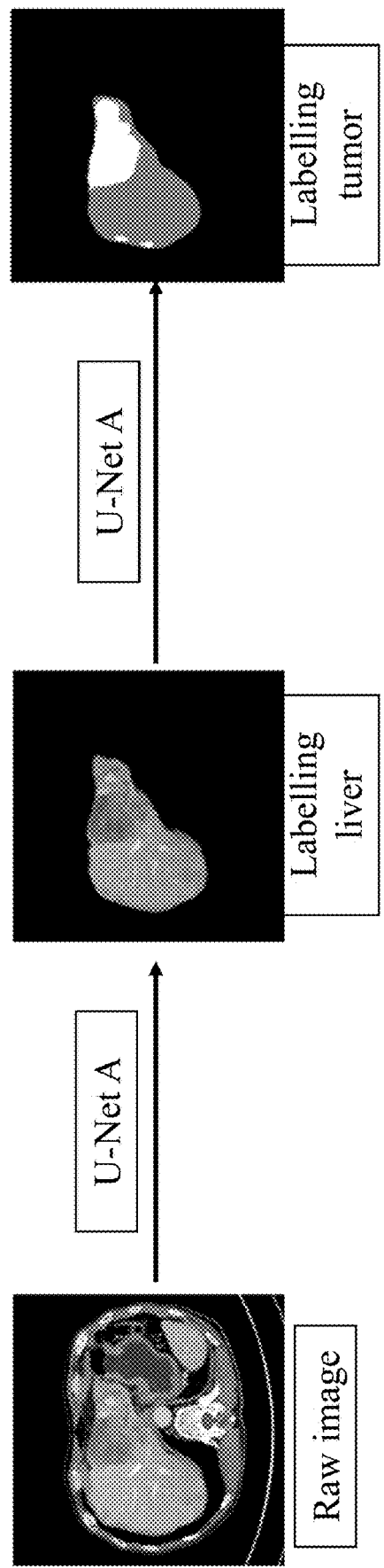
FIG. 10 is a flowchart illustrating assisted liver tumor labeling of example 1 in the present invention.

Please refer to FIG. 10, neural network models U-Net A and U-Net-B were established at radiomic feature extracting module A and radiomic feature extracting module B, respectively. An assisted labeling of the liver tumor was performed after, an AI-training module individually trained U-Net A and U-Net B based on an AI-assisting labeling model.

In example 1, U-Net A was trained by a liver region labeling model, which is established by integrating liver regions that experienced radiologists labeled at various time points. The preceding labeling was validated by 3D overlapping validation. On the other hand, U-Net B was trained by a liver region labeling model, which is established by integrating liver regions that experienced radiologists and hematologists labeled at various time points. The preceding labeling was also validated by 3D overlapping validation. In example 1, the radiomic feature extracting module A identifies a liver region from a raw image, and the radiomic feature extracting module B identifies a region of a tumor from the labeled region of a liver. Subsequently, the labeled region of a tumor was displayed on a multi-module management interface for users to review.

Example 2

Figures 11, 12:
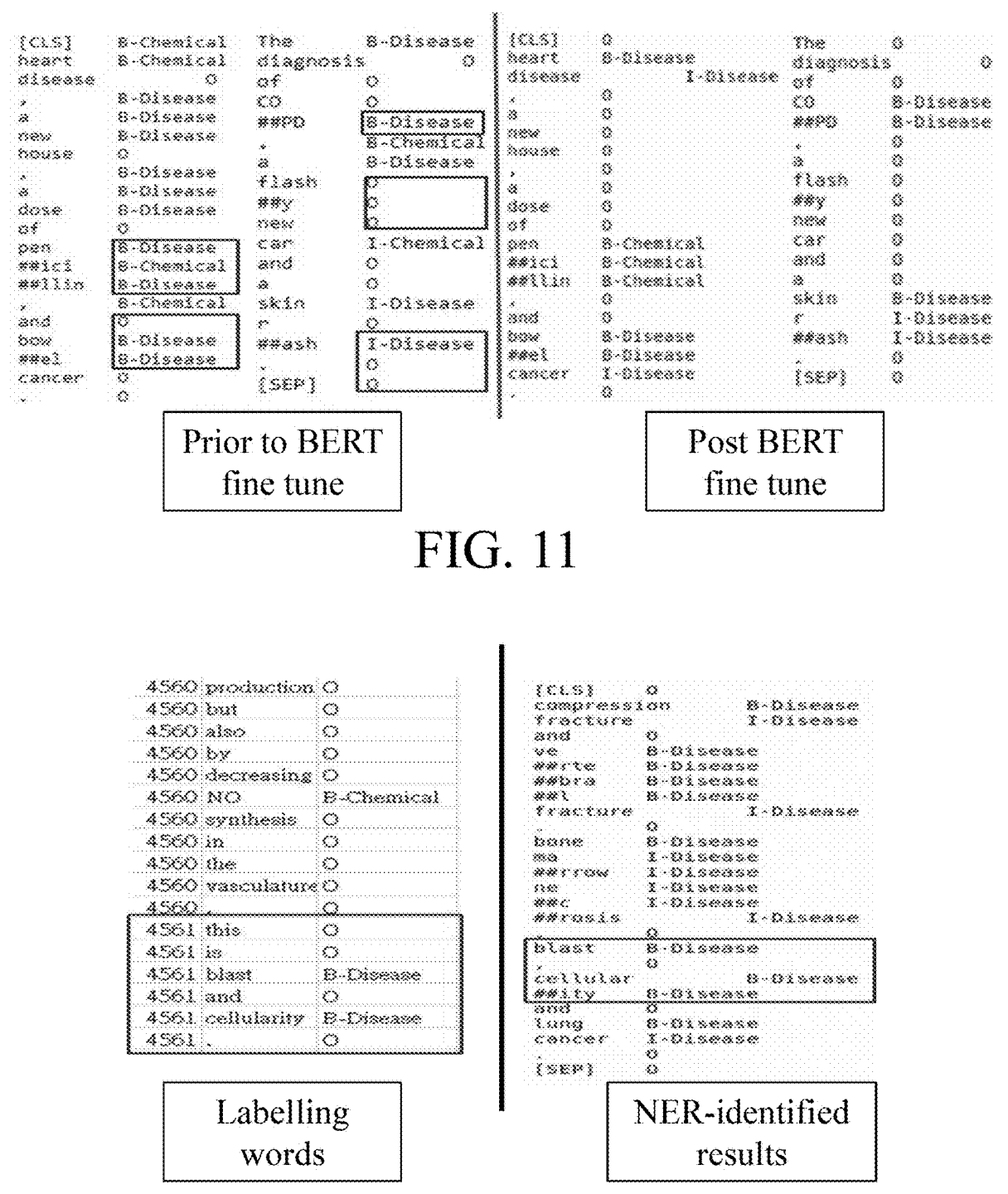

Please refer to FIG. 11, a test of text extraction is performed with radiology diagnosis reports. Keywords of the text extraction included parenchymal and nodules, and negative words were customized in a rule table. According to FIG. 11, as identified by a text extracting unit, the diagnosis report is not classified to the category of parenchymal since there was a negative word "no" ahead of parenchymal. The diagnosis report was organized into the category of the nodule.

Example 3

A test of time consumption of text categorization via the medical image project management platform was performed with 50,000 and 350,000 pathology reports, respectively. Execution periods were 5 minutes and 40 minutes, respectively, demonstrating text categorization with high efficiency.

Example 4

A training dataset BC5CDR was divided into ten datasets for K-fold Cross-Validation. Specifically, the $1^{st}$ dataset was considered a first validation dataset, and a validation error was computed. Subsequently, a second validation dataset was selected from the rest of the training datasets, while the first validation dataset passing validation returned to training datasets.

Please refer to TABLE 5, which illustrates precision values obtained by loop validation. The training dataset BC5CDR was divided into ten datasets, including nine training datasets and one validation dataset. Data validation training was performed with the API of Huggingface, and validation was repeated by maintaining nine training datasets and one validation dataset until every dataset was used as a validation dataset. Ten validation Errors were computed and represented in forms of precision values after ten times of execution. Ten precision values were averaged as a standard for model evaluation. The average precision value in the loop validation was 0.9880.

TABLE 5

| Loop | Precision |
| --- | --- |
| 1 | 0.9612 |
| 2 | 0.9766 |
| 3 | 0.9821 |
| 4 | 0.9863 |
| 5 | 0.9929 |
| 6 | 0.9952 |
| 7 | 0.9951 |
| 8 | 0.9966 |
| 9 | 0.9966 |
| 10 | 0.9974 |
| Ave. | 0.9880 |

Please refer to FIG. 6, which lists down identified items of BC5CDR training datasets and contents of the text to be tested by the NER reasoning model. Please refer to FIG. 11, which represents text label contents after validation. NER reasoning model would misjudge parts of words and phrases and deliver mislabel before being fine-tuned by BERT. NER reasoning model could deliver text labels in line with original literary meaning.

TABLE 6

| IDENTIFIED ITEMS | TEXT TO BE TESTED |
| --- | --- |
| B-Chemical | heart disease, a new house, a dose of |
| I-Chemical | penicillin, and bowel cancer. The diagnosis |
| O | of COPD, a flashy new car, and a skin. |
| I-Disease | |
| B-Disease | |

Example 5

Users customized training data by adding diagnostic information and labeling manually via the multi-module management interface and then performed BERT fine-tune to train the NER reasoning model using k-fold cross-validation. Please refer to FIG. 12, which indicates manual addition of "blast" and "cellularity" as words and labels. After k-fold cross validation training, the text extracting unit performed identification of text contents according to the NER reasoning model. "Blast bud cells" and "cellularity bone marrow cells" were identified, and words related to diseases were successfully identified from the text contents.

Example 6

Some text categorizing tests were performed with orthopedic diagnosis reports, and users customized rule tables as indicated by TABLE 7. Totally 50 diagnosis reports of spine fracture patients and another 50 non-spine-fracture patients were input to test the precision of diagnosis reports categorization by the medical image project management platform. The result showed that 50 diagnosis reports of fracture patients and 49 of non-spine-fracture patients were eventually categorized, indicating that only one non-spine-fracture diagnosis report was misidentified as a spine fracture diagnosis by the medical image project management platform.

TABLE 7

| Name of rule table: spine fracture | | | | |
|---|---|---|---|---|
| Report | Heading | Keywords | Return type | Negative |
| spine fracture_plain text report - test.xlsx | IMP, Impression | compression fracture r | Xlsx 1 | No, Without |

Advantages of the medical image project management platform in the present invention are further described below:
1. The present invention provides a one-station solution by incorporating data mining, application reviewing, progress management, image labeling, image integration, module training, E-alert, and E-assistance. The platform's operation is user-friendly and straightforward, and the process is easy and convenient.
2. The present invention performs the validation of medical image labeling quality. By calculating the overlapping rate, labeling quality is validated, which assists personnel involved in image labeling to adjust labeling patterns to optimize labeling quality.
3. Natural language processing (NLP) is applied in the present invention for disease categorizing. Data mining of medical reports and various images, words, and data files (DICOM, XML . . . etc.) in medical systems of a hospital (PACS, RIS, HIS, LIS, NIS . . . etc.) are also integrated, which assists users to retrieve data according to customized conditions swiftly and increases the availability of information regarding research topics of users.
4. AI-auto Annotation in the present invention allows intuitive labeling of PACS image, and radiomic features of the image could be automatically exported. Radiomic features generated automatically from PACS could be integrated and exported in a format such as DICOM or coordinates by the platform for various AI modules training. Besides, hospital-wide E-alert or E-assistance is further provided by the platform.
5. Extract-Transform-Load (ETL) is introduced in the present invention, and a web page-based Cross-modality Dashboard is also integrated. Visualized information renders project progress easy to track, and efficiency and precision of research and image interpretation are both significantly enhanced.

What is claimed is:

1. A medical image project management platform comprising:
   a project management module comprising:
   a multi-module management interface for inputting an image;
   a labeling unit connecting to the multi-module management interface for receiving the image to produce a first labeled image and a second labeled image from the image; and
   a radiomic feature extracting module comprising:
   an analysis unit connecting to the labeling unit for analyzing the first labeled image to output a first labeling unit, and analyzing the second labeled image to output a second labeling unit; and
   a feature extracting module connecting to the analysis unit for receiving the first labeling unit and the second labeling unit to perform a radiomic computation for outputting a radiomic feature.

2. The medical image project management platform as claimed in claim 1, wherein the platform further comprises a medical database connecting to the multi-module management interface.

3. The medical image project management platform as claimed in claim 2, wherein the medical database comprises PACS, RIS, HIS, LIS, NIS.

4. The medical image project management platform as claimed in claim 2, wherein the platform further comprises a text extracting module connecting to the multi-module management interface and the medical database for receiving a first diagnostic information from the multi-module management interface and extracting a first text information from the first diagnostic information.

5. The medical image project management platform as claimed in claim 4, wherein the text extracting module further analyzes the first text information referring to the medical database to obtain a first categorized diagnosis.

6. The medical image project management platform as claimed in claim 4, wherein the first diagnostic information comprises case history, medical record, a biochemical analysis report, a biochemical test report, a molecular test report, or a heading of a medical image.

7. The medical image project management platform as claimed in claim 4, wherein the platform further comprises an AI training module connecting to the labeling unit and the feature extracting module for reading the radiomic feature to train the labeling unit to establish an AI-assisting labeling model, wherein the labeling unit further connects to the medical database for input of a third image from the medical database to automatically output a third labeled image via the AI-assisting labeling model.

8. The medical image project management platform as claimed in claim 7, wherein the text extracting unit connects to the AI training module for reading the first categorized diagnosis to integrate the first categorized diagnosis and the radiomic feature into an AI medical diagnosis model.

9. The medical image project management platform as claimed in claim 7, wherein a diagnosis report is input through the multi-module management platform, wherein the diagnosis report comprises second diagnostic information and a fourth image; the project management module matches the diagnosis report to produce an auto-labeled report based on the AI medical diagnosis model, wherein the auto-labeled report comprises a second categorized diagnosis and a fourth labeled image.

10. The medical image project management platform as claimed in claim 9, wherein the multi-module management interface visualizes information of each module of the platform so that a user retrieves, labels, or searches for a medical data or a project progress, wherein the medical data comprises a medical image or a diagnostic information.

11. A labeling validation module comprising an overlapping validation model, wherein the labelling validation module connects the platform as claimed in claim 1 for receiving the first labeling unit and the second labeling unit to perform a validation computation to produce a first validation result based on the overlapping validation model.

12. The labeling validation module as claimed in claim 11, wherein the first validation result comprises a labeling qualification value, wherein the labeling qualification value comprises an ASSD (Average Symmetric Surface Distance) value, an IoU (Intersection over Union) value, a DICE coefficient, or a combination of two or more thereof.

13. The labeling validation module as claimed in claim 12, wherein the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

LU1 is the first labeling unit, and LU2 is the second labeling unit.

14. The labeling validation module as claimed in claim 12, wherein the IoU value is computed according to the following formula:

$$IOU(LU1, LU2) = \frac{|LU1 \cap LU2|}{|LU1 \cup LU2|};$$

and
the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

15. A method for medical image project management comprising a radiomic feature extracting process and a labeling qualification process, wherein the radiomic feature extracting process comprises steps of:
a first input step: inputting a first image via a multi-module management interface;
a labeling step: receiving the image and producing a first labeled image and a second labeled image of the image via a labeling unit;
an analysis step: analyzing the first labeled image to output a first labeling unit and analyzing the second labeled image to output a second labeling unit via an analysis unit; and
a feature extracting step: receiving the first labeling unit or the second labeling unit for performing a radiomic computation to output a radiomic feature via a feature extracting module; and
the labeling qualification process comprises receiving the first labeling unit and the second labeling unit for a validation computation to produce a first validation result via a labeling validation module, wherein the labelling validation module computes a labeling qualification value according to an overlapping validation model.

16. The method as claimed in claim 15, wherein the labeling qualification value comprises an ASSD value, an IoU value, a DICE coefficient, or a combination of two or more thereof.

17. The method as claimed in claim 16, wherein the ASSD value is computed according to the following formula:

$$ASSD = \frac{1}{|LU1| + |LU2|} \times \left( \sum_{x \in LU1} d(x, LU2) + \sum_{y \in LU2} d(y, LU1) \right);$$

LU1 is the first labeling unit, and LU2 is the second labeling unit.

18. The labeling validation module as claimed in claim 17, wherein the IoU value is computed according to the following formula:

$$IOU(LU1, LU2) = \frac{|LU1 \cap LU2|}{|LU1 \cup LU2|};$$

and
the DICE coefficient is computed according to the following formula:

$$DICE(LU1, LU2) = \frac{2|LU1 \cap LU2|}{|LU1| + |LU2|};$$

LU1 is the first labeling unit, and LU2 is the second labeling unit.

19. The method as claimed in claim 15, further comprising a text extracting process comprising steps of:
a second input step: inputting a first diagnostic information to the text extracting module via the multi-module management interface;
a text extracting step: extracting a first text information from the first diagnostic information via the text extracting module; and
a text categorizing step: matching the first text information referring to the medical database for outputting a first categorized diagnosis.

20. The method as claimed in claim 19, wherein the first diagnostic information comprises case history, medical record, a biochemical analysis report, a biochemical test report, a molecular test report, or a heading of a medical image.

* * * * *